US006398766B1

(12) United States Patent
Branch

(10) Patent No.: US 6,398,766 B1
(45) Date of Patent: Jun. 4, 2002

(54) EYE WASH SYSTEM

(75) Inventor: John D. Branch, Riverside, CA (US)

(73) Assignee: Vista Innovations, Inc., Riverside, CA (US)

( * ) Notice: Subject to any disclaimer, the term of this patent is extended or adjusted under 35 U.S.C. 154(b) by 0 days.

(21) Appl. No.: 09/472,248

(22) Filed: Dec. 27, 1999

(51) Int. Cl.[7] ........................ A61M 35/00; A61H 33/04

(52) U.S. Cl. ........................ 604/302; 604/294; 604/295; 604/298; 604/300

(58) Field of Search ................................ 604/294–302, 604/289; 128/200.23; 222/498, 527, 533, 556

(56) References Cited

U.S. PATENT DOCUMENTS

| | | | | | |
|---|---|---|---|---|---|
| 4,002,168 | A | * | 1/1977 | Peterson | 604/298 |
| 4,946,452 | A | * | 8/1990 | Py | 604/301 |
| 5,154,710 | A | * | 10/1992 | Williams | 604/301 |
| 5,163,929 | A | * | 11/1992 | Py | 604/298 |
| 5,178,613 | A | * | 1/1993 | Gibilisco | 604/295 |
| 5,207,657 | A | * | 5/1993 | Gibilisco | 604/295 |
| 5,267,986 | A | * | 12/1993 | Py | 604/294 |
| 5,401,259 | A | * | 3/1995 | Py | 604/294 |
| 5,429,621 | A | * | 7/1995 | Stahl | 604/298 |
| D368,774 | S | * | 4/1996 | Py | D24/113 |
| D374,719 | S | * | 10/1996 | Py | D24/120 |
| 5,578,019 | A | * | 11/1996 | Feldman | 604/295 |
| 5,607,410 | A | * | 3/1997 | Branch | 604/302 |
| 5,795,342 | A | * | 8/1998 | Shapiro et al. | 604/300 |
| 6,053,433 | A | * | 4/2000 | Py | 239/574 |
| 6,213,982 | B1 | * | 4/2001 | Py | 604/186 |

* cited by examiner

*Primary Examiner*—Kim M. Lewis
(74) *Attorney, Agent, or Firm*—Milton M. Field

(57) ABSTRACT

An eye wash system including a first base member slidable on a second base member from a retracted storage position to an extended operative position. One base member has an eye piece on its front end. The other base member pivotally supports a coupling assembly on which a flexible squeeze bottle is attached. A fluid line from the coupling assembly leads to a spray nozzle mounted on the front end of the other base member. A seal structure on the back side of the eye piece is moved rectilinearly into engagement with the spray nozzle to seal it when the one base member is in its retracted storage position. The bottom wall of the other base member has a resilient tongue with a detent ridge at its free end. Detent grooves on the coupling assembly cooperate with the detent ridge to latch it in the vertical or horizontal positions of the coupling assembly. Modifications of the spray nozzle include means for metering the liquid to be sprayed.

24 Claims, 6 Drawing Sheets

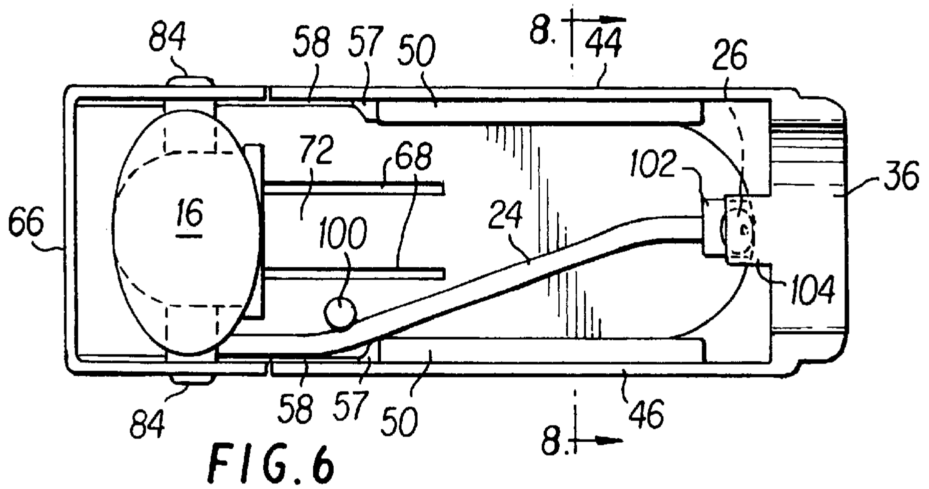
FIG. 6
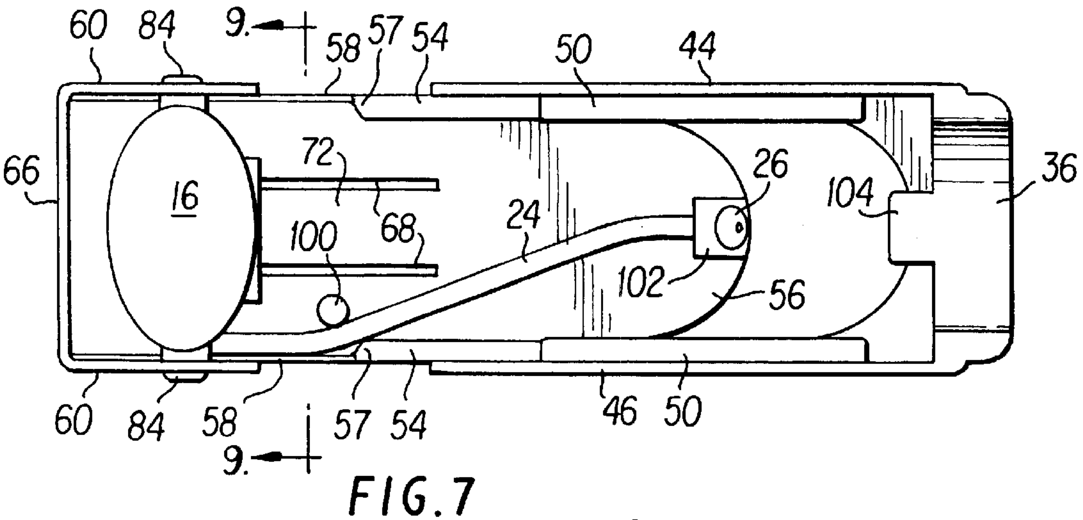
FIG. 7
FIG. 8
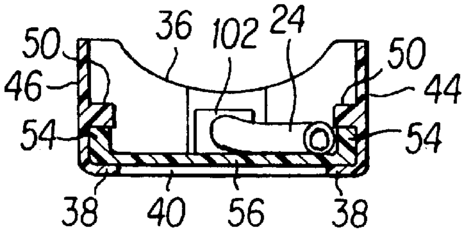
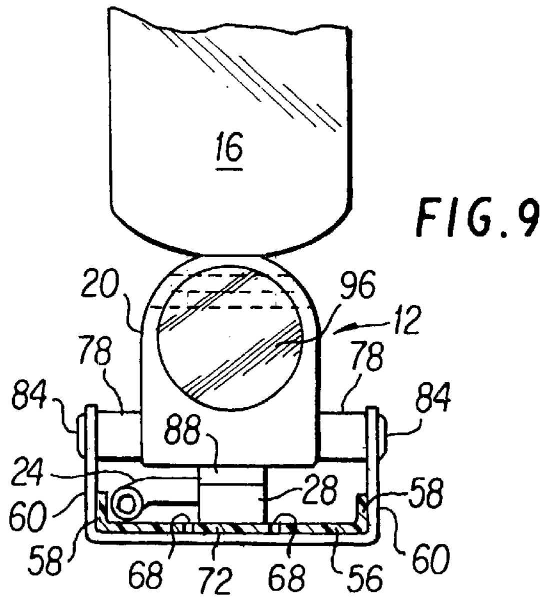
FIG. 9

EYE WASH SYSTEM

BACKGROUND OF THE INVENTION

1. Field of the Invention

This invention relates to an eye wash system, and, more particularly, to a portable, compact, low-cost eye wash system which can be used in an emergency.

2. Description of the Prior Art

My U.S. Pat. No. 5,607,410 shows portable eye wash systems intended for use in an emergency. These systems include a fluid reservoir having a flexible squeeze container mounted on a housing and a trough pivoted at one end to the housing. An eye piece at the other end of the trough is engaged with the user's face adjacent his eye. For enabling the user to view his eye, a mirror is mounted on the housing. A fluid line extends from the housing along the trough to a spray outlet on the trough positioned to spray the user's eye. The trough may be pivoted to an operative position perpendicular to the axis of the reservoir or to a storage position in which the reservoir rests in the trough. The flow of liquid may be cut off by means of a lever-operated valve in the housing or by a closure cap mounted on an arm extending from the housing along the squeeze bottle and engaging the spray outlet when the trough is in the storage position. In order to provide a satisfactory seal, a rubber sealing cushion is used as the closure cap.

Petterson U.S. Pat. No. 4,002,168, FIG. 19, shows an eye wash dispenser in which a pivoted trough seals the orifice.

It is sometimes required that the eye wash system dispense a limited quantity of a prescription liquid. Py U.S. Pat. No. 5,163,929 shows an ocular vial for applying a 20 microliter drop of medicament into the user's eye. A supply cavity feeds the liquid to a drop cavity which is then closed by a piston. When the piston is depressed, the drop is applied through an orifice. This device is a complex eye dropper which does not spray the liquid into the user's eye and includes no means for positioning a spray outlet relative to the user's eye. A screw-on cap includes a nipple for sealing the orifice.

Py U.S. Pat. No. 5,267,986 also shows a dispenser including a drop cavity which holds a predetermined volume of fluid to be emitted in the form of a drop. A spring causes expansion of the dispenser to emit a drop through the nozzle. A projecting finger is engaged with the user's eyelid.

Py U.S. Pat. No. 4,946,452 also uses an eyepiece for properly positioning a medicament dispenser. An outer housing is slidably engaged over an inner housing to force the closed end of the vial towards the nozzle and displace a predetermined volume of medicament through the nozzle.

Gibilisco U.S. Pat. Nos. 5,207,657 and 5,178,613 show dispensers for ophthalmic liquids which have movable tops that rotate to seal the dispensing tips. In Gibilisco U.S. Pat. No. 5,181,634, a cap moves up and down and has a flexible shield member which bends as the cap moves down to close the aperture.

Shapiro et al. U.S. Pat. No. 5,795,342 show an ocular irrigation device including a sliding member carrying a hollow-arcuate member with dispensing orifices and a channel member carrying an eyelid engaging member.

Feldman U.S. Pat. No. 5,578,019 provides an eye drop applicator having an eyelid retractor and a pivoted closure.

Other eye drop dispensers of interest are shown in U.S. Pat. Nos. 5,429,621; 5,154,710; 5,401,259; 3,193,575; and 2,736,316.

SUMMARY OF THE INVENTION

It is an object of this invention to provide an improved portable, low cost eye wash device which can be used in an emergency to flush an eye or to apply a predetermined quantity of an ophthalmic medicament to an eye.

In the eye wash systems of my U.S. Pat. No. 5,607,410, the spray orifice is sealed by a closure cap which engages the spray outlet after rotating the fluid reservoir into the trough. It is an object of the present invention to provide improved means for sealing the spray outlet.

Because it is sometimes necessary to dispense a limited quantity of an ophthalmic medicament, it is an object of the invention to provide an eye wash system having improved metering means to limit the quantity of the liquid dispensed.

An eye wash system of the present invention includes first and second base members, one of which is slidable on the other, to form a trough-shaped structure. An arcuate eye piece is formed at the front end of the first base member for positioning the system for flushing a user's eye. The eye wash liquid is supplied from a coupling assembly, comprising a liquid receiving housing into which a flexible squeeze bottle is threaded, the housing being pivotally mounted at the rear end of the second base member. A fluid line runs from the housing along the second base member to a spray outlet near the front end of the second base member and is positioned to spray the liquid into the user's eye when the eyepiece is engaged with the user's face along an arc below the user's eye. The housing may be pivoted to an operative position perpendicular to the base members and to a storage position in which the housing and bottle lie in the trough parallel to the base members. A closure cap is formed on the front end of the first base member just behind the eye piece and facing to the rear at the same level as the spray outlet. When the first base member is slid to its forward position with the housing pivoted to its operative position perpendicular to the trough and with the eye piece is positioned against the user's face below his eye, the spray outlet is properly positioned to spray the user's eye. When the first base member is slid to its rearward position, and the housing is pivoted to its storage position, the spray outlet is moved into engagement with the closure cap on the first base member. Because the first base member slides with a precise rectilinear movement, a good seal is obtained between the sealing cap and the spray orifice. In order to maintain the first base member in its forward position with the spray orifice properly positioned to spray the liquid into the user's eye and in its rearward position with the closure cap held against the spray orifice, cooperating retaining means are provided on the first and second base members. The first base member has a bottom wall having an opening the rear side of which is closed by a bridge member. The second base member has a bottom wall, the bottom side of which has a recessed section with a boss forming fore and aft grooves. The boss is positioned on a resilient tongue formed by slots through the bottom wall of the second base member. When the first base member is slid to its forward position, the bridge member seats in the fore groove to block further sliding motion. When the first base member is slid to its retracted position, the bridge member seats in the aft groove to block further sliding motion and maintain the cover cap in engagement with the spray outlet.

Detent means latches the housing to its operative position perpendicular to the base members or in to its storage position in the trough parallel to the base members. To this end, the coupling assembly includes a retaining structure below the housing when the housing is in its operative position perpendicular to the base members. A pair of detent grooves are formed on the retaining structure, and a detent ridge is formed on the upper side of, and at the free end of, the resilient tongue formed on the bottom wall of the second base member. When the housing is in its operative position, the detent ridge seats in one of the grooves to hold the housing in the operative position. When the housing is in its storage position, it is held by the detent ridge engaged in the other detent groove.

To enable the user to view his eye with the eye piece engaged with his face and the eye wash system in position for use, a mirror is fastened to the housing on a wall facing the eye piece.

While the eye wash system of the invention may be used to rinse contaminants from the user's eye, it also has utility for applying a limited quantity of an ophthalmic medicament, such as a prescription medicine. For this use of the system, it is necessary to provide metering means for dispensing a limited quantity of the liquid. In a first embodiment of metering means, the spray nozzle includes a chamber within which a polyvinyl chloride or silicone rubber disk is movable along a guide pin aligned with the tubing conveying the liquid from the bottle and the nozzle orifice. A spring biases the disk to close the tubing. When the user squeezes the bottle, the pressure of the fluid moves the disk towards the nozzle orifice permitting a limited quantity of the liquid to flow from the tubing around the disk and out the nozzle orifice.

In a second embodiment of the metering means, a cylindrical nozzle chamber is provided to receive the liquid from the fluid line. The chamber has a conical end portion with the spray outlet located at the apex thereof. A flexible disk is located in the cylindrical nozzle chamber having an outer diameter substantially equal to the inner diameter of the chamber. The edge of the disk has apertures formed or cut out of the disk. When the liquid is dispensed through the fluid line, a small amount of the fluid is forced around the disk through the cutouts. The bulk of the fluid then distorts the central part of the disk and pushes the central part against the conical end surface of the chamber to close the spray outlet at the apex of this surface. In this way, a metered dose of eye drops is sprayed into the user's eye. The corners of the cutouts on the disk may be folded forwardly to provide extra elastic spring to the disk.

Other objects, features and advantages of the invention will become apparent from the following detailed description and drawings.

BRIEF DESCRIPTION OF THE DRAWINGS

FIG. 6 is a plan view of the eye wash system of FIG. 4;

FIG. 7 is a plan view of the eye wash system of FIG. 5;

FIG. 8 is a cross-sectional view along the line 8—8 of FIG. 6;

FIG. 9 is a cross-sectional view along the line 9—9 of FIG. 7;

DETAILED DESCRIPTION

Figure 1:
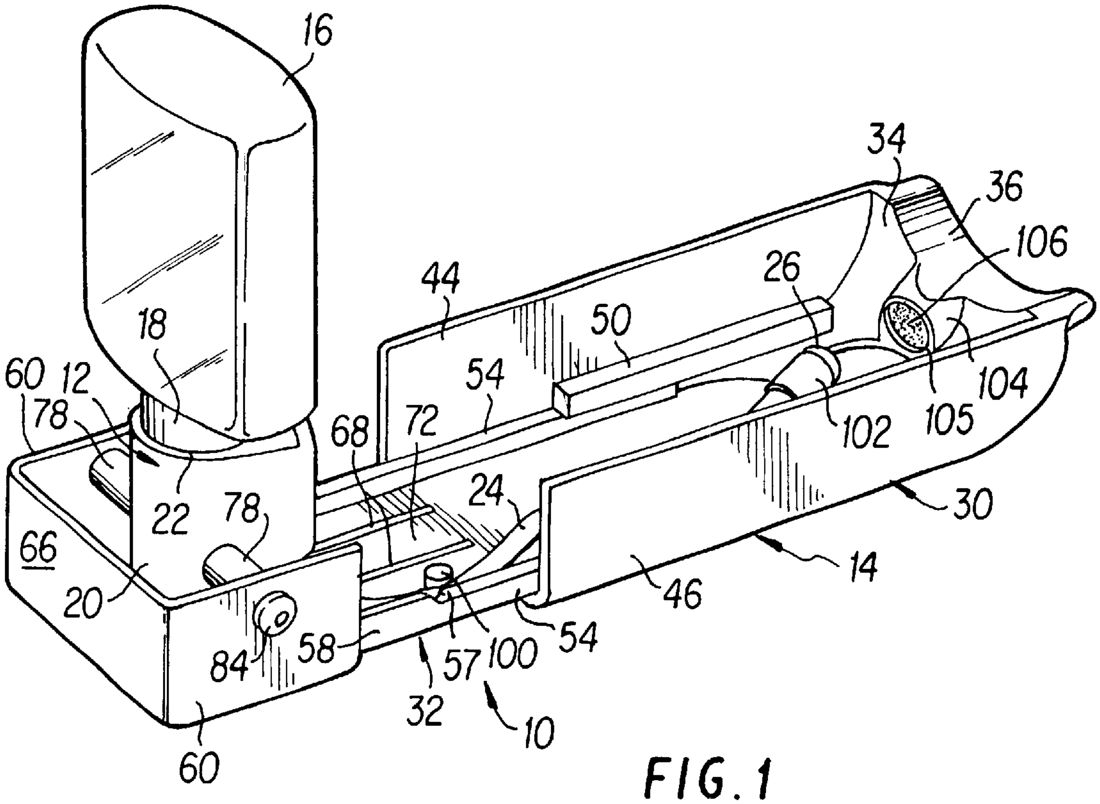
FIG. 1 is a perspective view of an eye wash system of the invention showing the system ready for use with the housing assembly and bottle in their operative position and the base assembly in its extended operative position.

An eye wash system 10 the invention includes a coupling assembly 12 and a base assembly 14. A flexible squeeze bottle 16 supplies an eye wash liquid or an ophthalmic medicament to housing 20 of coupling assembly 12. Bottle 16 has a threaded neck 18 which is received in a complementary threaded inlet opening 22 of housing 20.

The liquid is fed from housing 20 through a fluid line 24 to a spray nozzle 26, from which the liquid is dispensed as a spray into the eye of a user. Coupling assembly 12 includes a lower retaining structure 28 which depends from the bottom side of housing 20 when the assembly is positioned vertically with bottle 16 above coupling assembly 12. A fluid passageway 27 (shown schematically in FIG. 2) extends through retaining structure 28 from housing 20 to fluid line 24. As will be explained below, retaining structure 28 includes means for latching coupling assembly 12 either in its horizontal storage position or its vertical operative position.

Figure 3:
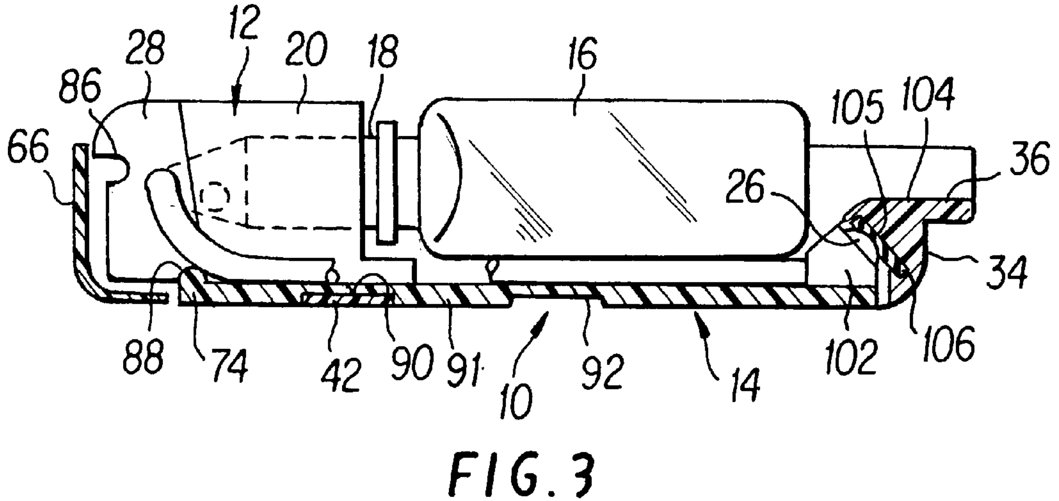
FIG. 3 is a side elevation view, partially in section, of the eye wash system of FIG. 2.
Figure 4:
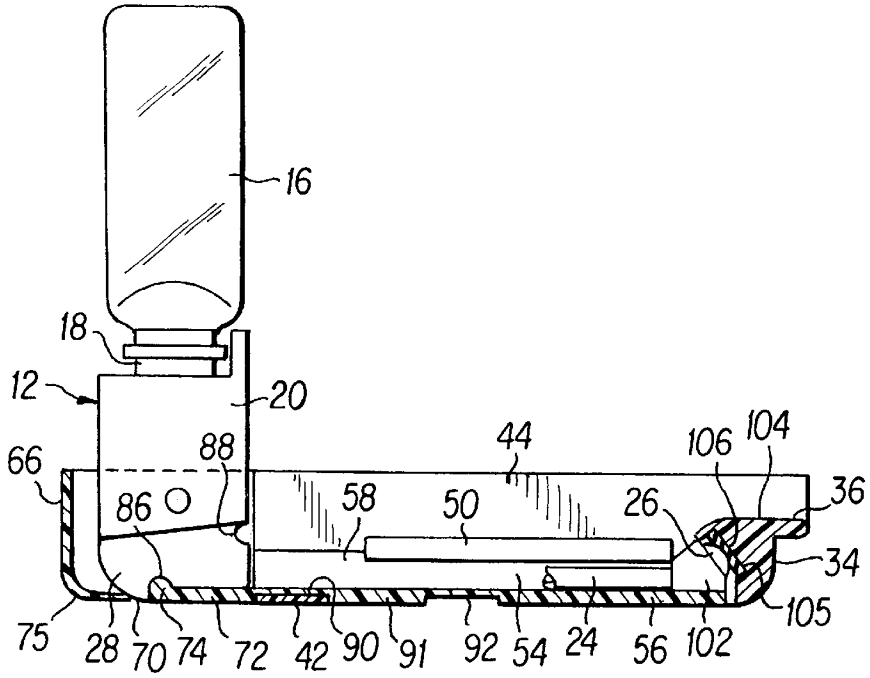
FIG. 4 is a side elevation view, partially in section, of the eye wash system of FIG. 2 with the housing and bottle pivoted to their operative position perpendicular to the base members.
Figure 5:
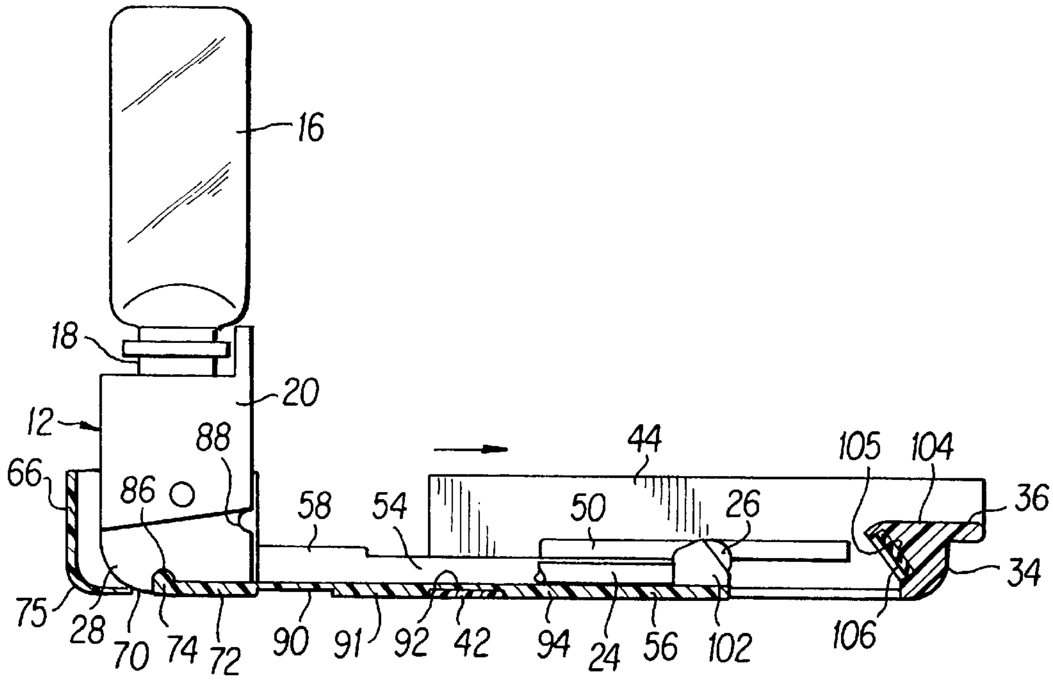
FIG. 5 is a side elevation view, partially in section, of the eyewash system of FIG. 4 in its operative position with one of the base members slid forwardly.
Figure 10:
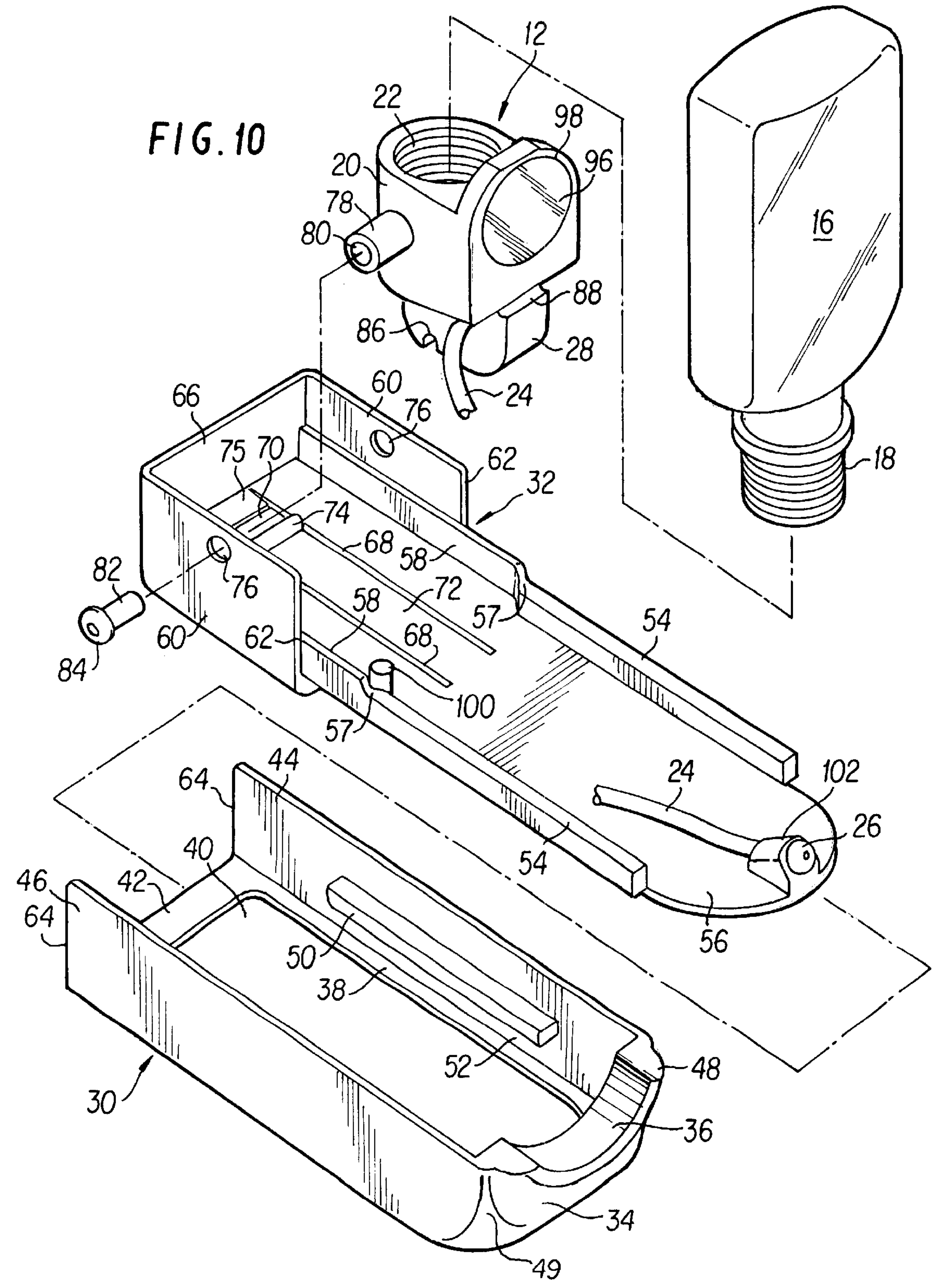
FIG. 10 is an exploded view of the eye wash system of the invention.

Base assembly 14 includes a first base member 30 slidably mounted on a second base member 32 from a retracted storage position, as shown in FIGS. 2, 3, 4 and 6, to an extended operative position, as shown in FIGS. 1, 5 and 7. Base member 30 has a front wall 34, the top of which is shaped to form an arcuate eye piece 36. A bottom wall 38 frames a central opening 40, the rear end of which is closed by a bridge member 42. A pair of side walls 44 and 46 rise from bottom wall 38 along the sides of base member 30 and meet front wall 34 to form corners 48 and 49. As is best seen in FIG. 10, the rear side of base member 30 is open above bridge member 42. As most clearly seen in FIGS. 1, 8 and 10, a pair of guide projections 50 are formed on side walls 44 and 46 spaced above and parallel to bottom wall 38 to form guide slots 52.

As will be presently described, guide rails 54 are formed on second base member 32 and are so dimensioned that they slidably fit in guide slots 52. As most clearly seen in FIG. 10, base member 32 has a bottom wall 56 on opposite sides of which rails 54 rise to form, in effect, low side walls. At the rear ends of rails 54 are tapered transition sections 57, after which there are wall extensions 58 which are somewhat thinner and taller than rails 54. Because tapered sections 57 extend a bit above the lower sides of projections 50, they act as abutments to limit the backward sliding movement of base member 30. At the rear end of base member 32, a U-shaped wall is formed with side walls 60 positioned over the outer sides of wall extensions 58 to form with forward edges 62 additional abutments to limit rearward sliding movement of base member 30 as the rearward edges 64 of walls 44 and 46 of base member 30 abut wall edges 62. A rear wall 66 completes the U-shaped wall.

In order to provide for resilient detent action, a pair of parallel slots 68 are provided through bottom wall 56 of base member 32. These begin shortly in front of the rearward ends of rails 54 and extend rearwardly to join an opening 70 which extends from slot to slot and with the slots forms a resilient tongue 72. A detent ridge 74 is formed on the upper side of and at the rear end of tongue 72 adjacent opening 70. To the rear of opening 70, there is a wall section 75 which is thinner than the rest of bottom wall 56 to allow more room for the detent operation to be described below.

Coupling assembly 12 is pivotally mounted between side walls 60. To this end, pivot holes 76 are provided through walls 60 and pivot arms 78 extend from each side of housing 20. Pivot arms 78 are tubular, providing pivot pin receiving openings 80. Pivot pins 82, which are formed of stainless steel tubes and have end flanges 84, extend through openings 76 into the openings 80 in pivot arms 78 to provide pivotal support for coupling assembly 12.

In order to latch coupling assembly 12 in its horizontal storage position parallel to base members 30 and 32 and in its vertical operative position perpendicular to the base members, retaining structure 28 is provided with a detent groove 86 on its bottom side when coupling assembly 12 is in its vertical position with bottle 16 above coupling assembly 12, as shown in FIGS. 4 and 5, and with a detent groove 88 on its bottom side when coupling assembly 12 is rotated to its horizontal storage position as shown in FIG. 3.

When coupling assembly 12 is rotated to its operative position, as shown in FIG. 4, from its storage position as shown in FIG. 3, retaining structure 28 forces the end of flexible tongue 72 and ridge 74 downwardly allowing structure 28 to slide over ridge 74 until ridge 74 snaps into groove 86. This will latch coupling assembly 12 in its vertical position. When coupling assembly 12 is rotated to return to its horizontal position, retaining structure 28 again depresses ridge 74 and tongue 72 allowing structure 28 to again slide over ridge 74 until ridge 74 snaps into groove 88 to latch coupling assembly 12 in its horizontal position as seen in FIG. 3.

So that base member 30 can be latched in its extended or retracted positions, the outer, downwardly facing side of bottom wall 56 of base member 32 is provided, as seen in FIGS. 3, 4, and 5, with latching grooves 90 and 92 which are separated by a boss 91. Groove 90 and most of boss 91 are, in fact, on the bottom side of flexible tongue 72, while groove 92 is formed on the bottom side of bottom wall 56 before the beginning of slots 68. Turning to FIGS. 3 and 4, with the base member 30 in its retracted storage position, bridge member 42 of base member 30 snaps into groove 90 to retain base member 30 in this position. When, however, base member 30 is slid forwardly to its extended position, bridge member 42 slips out of groove 90 and snaps into groove 92, as seen in FIG. 5. In this position, the front section 94 of bottom wall 56 abuts bridge member 42 and blocks further forward sliding movement of base member 30. By virtue of the flexibility of tongue 72, bridge member is able to slip out of groove 90 when base member 30 is slid forwardly and to slip out of groove 92 when base member 30 is slid rearwardly.

To enable the user to observe his eye when he sprays the eye wash liquid by squeezing flexible bottle 16, a mirror 96 is positioned in a recess 98 provided on the side of housing 20 which faces eye piece 36 when coupling assembly 12 is rotated to its vertical position. The mirror is affixed with any suitable adhesive.

Figure 2:
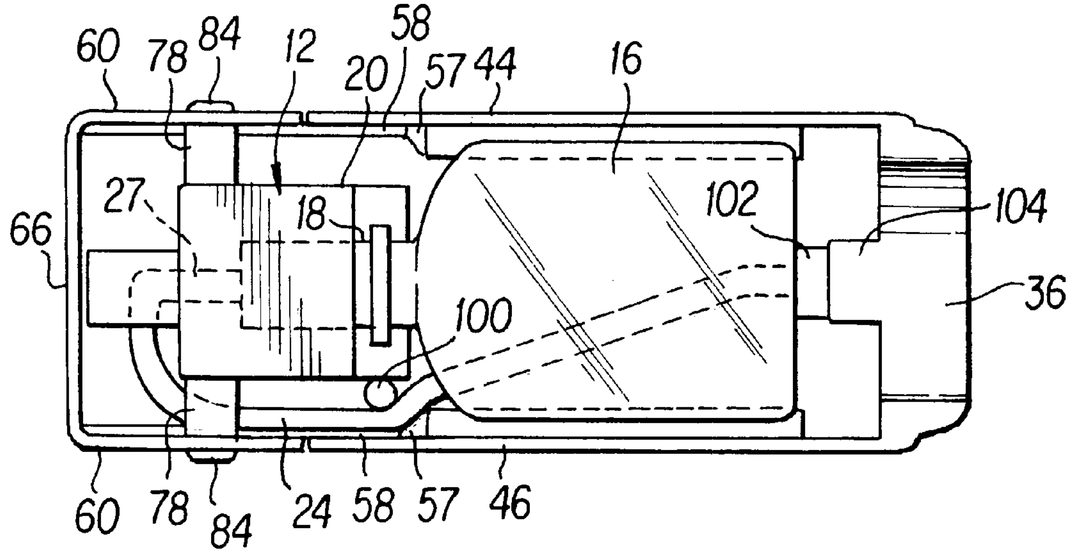
FIG. 2 is a top plan view, partially schematic, of an eye wash system of the invention in its storage position with the housing and bottle lying within the trough formed by the two base members.

As seen in FIGS. 2 and 3, the liquid passageway 27 through coupling assembly 12 terminates on the right side of retaining structure 28. Fluid line 24 is affixed in the passageway by means of a suitable adhesive and then extends along the right side of base member 32. A fluid line securing pin 100 is formed on bottom wall 56 adjacent to transition wall section 57, being spaced from wall section 56 by a distance which permits fluid line to be wedged between pin 100 and wall section 57. Fluid line 24 then continues to spray nozzle 26 which is mounted on the front end of bottom wall 56 by means of a mounting cowl 102.

In order to seal spray nozzle 26 when the system is in its retracted storage position, as shown in FIGS. 2, 3, 4 and 6, a stopper projection 104 on the rear side of eye piece 36 provides a stopper surface 105 on which a sealing disk 106 of silicone rubber is adhesively affixed. When base member 30 is slid to its retracted position, sealing disk 106 engages spray nozzle 30 to seal its opening. Since the movement of sealing surface 105 as base member 32 is slid rearwardly is rectilinear, sealing disk 106 firmly and accurately engages the opening from spray nozzle 30 effectively sealing it. Due to the latching action of bridge member 42 seated in groove 90, spray nozzle 30 is kept in firm engagement with sealing disk 106.

Figure 11:
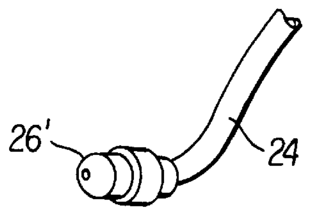
FIG. 11 is a perspective view of a first embodiment of a metering spray nozzle of the eye wash system of the invention with the support cowl removed.
Figure 12:
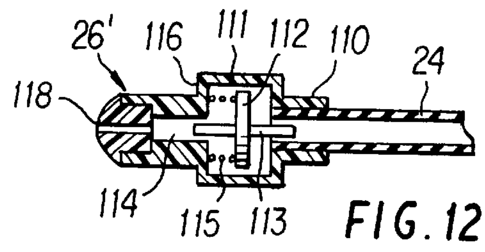
FIG. 12 is a diagram in section illustrating the internal construction of the spray nozzle of FIG. 11.

In order to facilitate single drop dosing when a ophthalmic medicine is dispensed, two embodiments of metering spray nozzle are provided. One embodiment of the metering spray nozzle 26' is shown in FIGS. 11 and 12. Nozzle 26' has an inlet sleeve 110 and fluid line 24 is inserted in sleeve 110 and affixed therein by a suitable adhesive. Inlet sleeve 110 leads to a disk chamber 111 of greater diameter within which a valve disk 112, which is formed of PVC or silicone rubber, is positioned. Disk 112 is slidably mounted on a guide pin 113 which fits loosely in the end of fluid line 24 and an outlet chamber 114. A spring 115 is mounted between a wall 116 of chamber 111 and disk 112. When the user squeezes flexible bottle 16, the liquid flows through fluid line 24 and forces disk 112 to overcome the bias of spring 115 and close outlet opening 118, permitting only a limited quantity of the liquid to be sprayed from discharge opening 118.

Figure 13:
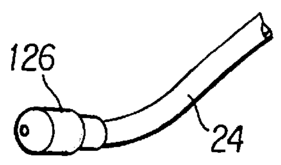
FIG. 13 is a perspective view of a second embodiment of a metering spray nozzle of the eye wash system of the invention with the support cowl removed.
Figure 15:
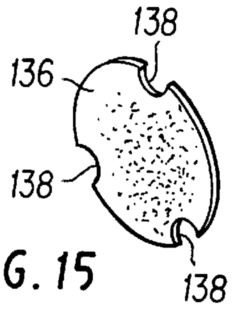
FIG. 15 is a perspective view of a metering disk used in the embodiment of FIG. 14.
Figure 14:
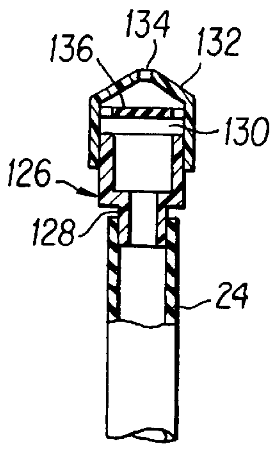
FIG. 14 is a diagram in section illustrating the internal construction o the spray nozzle of FIG. 13 before liquid flows to the spray nozzle.
Figure 16:
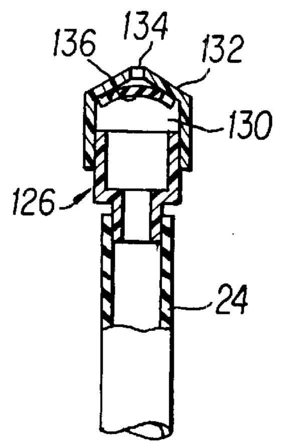
FIG. 16 is a diagram illustrating the internal construction of the spray nozzle of FIG. 14 when the liquid flowing into the spray nozzle has forced the disk to close the nozzle orifice.

Another embodiment of metering spray nozzle 126 is shown in FIGS. 13–15. Fluid line 24 is slipped over an inlet tube 128 which conveys the liquid into a cylindrical chamber 130 having a conical end wall 132 with an outlet opening 134 at its apex. A flexible disc 136 of mylar, rubber or silicone rubber has peripheral apertures 138. When the user squeezes the flexible bottle 16, the liquid enters chamber 130 and a small amount is forced around disk 136 through apertures 138. The force of the liquid then pushes disk 136 and distorts the central portion of disk 136 over outlet opening 134 to shut off further flow as shown in FIG. 16. This permits metered dosing of eye drops and the like.

Figure 18:
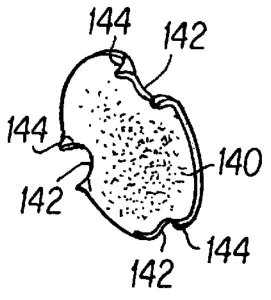
FIG. 18 is a perspective view of the metering disk used in the variant of FIG. 15.
Figure 17:
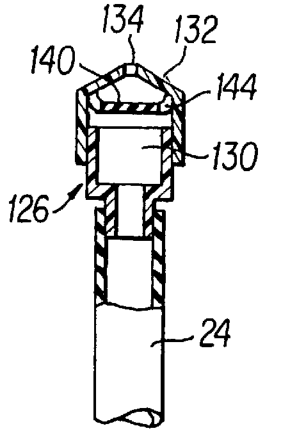
FIG. 17 is a diagram in section illustrating the internal construction of a variant of the spray nozzle of FIG. 14.

A variant of this embodiment is shown in FIGS. 17 and 18. Disk 140 is substituted for disk 136. Peripheral apertures 142 are again provided, but the corners 144 of the aperture are folded forward to give extra elastic spring to the disk. This permits more efficient metering of eye drops.

Coupling assembly 12, base member 30, and base member 32 are molded of ABS or polypropylene. Squeeze bottle 16 is formed of either high or low density polyethylene, low density polyethylene being preferred. Fluid tube 24 is made of polyvinyl chloride or Tygon tubing. As mentioned above, seal disk 106 is formed of silicone rubber. Stainless steel pivot pins 82 are glued in pivot arms 78 by dripping pins 82 in a solvent of cyclohexanane which acts as an adhesive.

When, as shown in FIG. 2, the device is in its storage configuration with coupling assembly 12 and squeeze bottle 16 pivoted to their horizontal position and with base member 30 slid to its retracted position, coupling assembly 12 and squeeze bottle 16 are positioned in a trough-like structure, surrounded by walls on three sides. Walls 60 and 66 of base members 32 border the rear end, while walls 44 and 46 abut forward edges 62 of walls 60. The bottom side is closed by bottom wall 56 of base member 32.

The device is normally kept in this storage position as shown in FIG. 2 and is retained in this position by ridge 74 on flexible tongue 72 engaged in detent groove 88 of retaining member 28 as shown in FIG. 3. Base member 30 is latched in its retracted position by the seating of bridge member 42 in groove 90. When base member 30 is so latched in its retracted position, seal surface 105 and sealing disk 106 press against the opening of spray nozzle 26 to seal it and prevent leakage therefrom.

When the user wishes to use the device, he or she rotates squeeze bottle 16 and coupling assembly 12 to the vertical position as shown in FIG. 4. As the structure is rotated, ridge 74 slips out of detent groove 88, slides along the surface of retaining member 28, and seats in detent groove 86 to latch coupling assembly 12 in its vertical position. The user then pulls base member 30 forwardly causing bridge member 42 to slip out of groove 90, slide along the bottom side of bottom wall 56, and seat in groove 92 to retain base member 30 in its extended operative position. The device is now ready for use.

The user positions eye piece 36 on his or her face just below the eye to be treated. By observing his or her eye in mirror 96, the user can properly position eye piece 36. With the eye piece in place, the user then squeezes squeeze bottle 16. If a normal spray nozzle 26 is used, the liquid then flow through fluid passageway 27 in coupling assembly 12 to enter fluid line 24, and through fluid line 24, to spray nozzle 26. The fluid then sprays out of spray nozzle 26 to enter and wash the user's eye. If a metering spray nozzle 26' as shown in FIGS. 11 and 12 or a metering spray nozzle 126 as shown in FIGS. 13–18 is used, a limited dosage quantity is sprayed from the spray nozzle into the user's eye as explained above.

I claim:

1. An eye wash system, comprising;

a first base member;

a second base member slidable on said first base member, said base members having corresponding front and rear ends;

eye piece means formed at the front end of said first base member for positioning said system for flushing a user's eye when said eye piece means engages a user's face;

a coupling assembly mounted on said second base member, said coupling assembly having means for receiving an eye wash liquid;

a fluid line mounted on said second base member for conveying the eye wash liquid from said coupling assembly to a spray outlet at said front end of said second base member;

closure means at said front end of said first base member, said closure means being adapted to engage and close said spray outlet;

slide means for enabling said first base member to slide on said second base member from a forward position at which said spray outlet is positioned to spray eye wash liquid into the user's eye to a rearward position at which said closure means engages said spray outlet to close said spray outlet.

2. The eye wash system according to claim 1, wherein said coupling assembly is pivoted to said second base member adjacent said rear end of said second base member, being pivotal to a first vertical operative position or to a second horizontal storage position.

3. The eye wash system according to claim 2, wherein an eye wash liquid container is coupled to said coupling assembly to feed the eye wash liquid to said means for receiving an eye wash liquid.

4. The eye wash system according to claim 3, wherein said first and second base members are nested to from a trough.

5. The eye wash system according to claim 4, wherein said container lies within said trough when said housing is in said storage position.

6. The eye wash system according to claim 3, wherein said container is a flexible squeeze bottle.

7. The eye wash system according to claim 3, further comprising flexible detent means on said second base member to hold said coupling assembly in said vertical operative position or said horizontal storage position.

8. The eye wash system according to claim 3, further comprising means for attaching a mirror to said coupling assembly, said mirror, when said coupling assembly is in said vertical operative position, facing said eye piece, means so that the user may view his eye.

9. The eye wash system according to claim 1, wherein said spray outlet is formed on a nozzle housing, said nozzle housing comprising metering means for limiting the quantity of the liquid dispensed through said spray outlet.

10. The eye wash system according to claim 9, wherein said metering means comprises a flexible disk within said nozzle housing and wherein said flexible disk has peripheral indentations.

11. The eye wash system according to claim 10, wherein said nozzle housing has a conical end wall with said spray outlet at the apex of said conical end wall and a cylindrical chamber, the outer diameter of said disk being substantially equal to the inner diameter of said cylindrical chamber, said fluid line being adapted to dispense the eye wash liquid to said cylindrical housing, whereby when said cylindrical housing receives said eye wash liquid, some of the liquid flows through said indentations and said spray outlet and the pressure of the liquid on said disk forces said disk against said conical end wall to close said spray outlet, whereby only a limited quantity of the liquid is dispensed through said spray outlet.

12. The eye wash system according to claim 11, wherein said peripheral indentations have corners which are folded over toward said spray outlet to increase the springiness of said disk.

13. The eye wash system according to claim 9, wherein said metering means comprises fluid responsive biased valve means.

14. The eye wash system according to claim 13, wherein said biased valve means comprises a disk movable along a guide pin aligned with said fluid line and said spray outlet and spring means biasing said disk to close said fluid line, said disk being pushed along said guide pin by fluid in said fluid line to allow a limited quantity of the liquid to be dispensed through said spray outlet.

15. The eye wash system according to claim 1, wherein said second base member has a bottom wall with a flexible detent means formed on said bottom wall, and wherein said coupling means comprises a retaining member, said retaining member having first means for cooperating with said flexible detent means to retain said coupling means in said vertical operative position and second means for cooperating with said flexible detent means to retain said coupling means in said horizontal storage position.

16. The eye wash system according to claim 1, wherein said first and second base members comprise retaining means to retain said first base member in said forward position or in said rearward position.

17. The eye wash system according to claim 1, wherein said first base member has a bottom wall, said bottom wall having an aperture with a bridge member at the rear end of said first base member closing said aperture, and wherein said second base member has a bottom wall having a recess formed on its bottom side and a boss projecting from said recess to form a pair of shallow grooves, respectively fore and aft of said boss on said bottom side, said shallow grooves having substantially the same width as said bridge member, whereby said bridge member seats in the rearward groove when said first base member is slid its rearward position to retain said first base member in said rearward position and said closure means in engagement with said spray outlet, and in the forward groove when said first base member is slid to its forward position to retain said first base member in said forward position.

18. The eye wash system according to claim 17, wherein said bottom wall of said second base member comprises slots defining a resilient tongue member, said boss projecting from the bottom side of said resilient tongue member.

19. An eye wash system, comprising:

a first base member;

a second base member;

supply means mounted on said second base member for supplying an eye wash liquid;

a spray outlet mounted on said second base member;

means for feeding the eye wash liquid from said supply means to said spray outlet;

closure means mounted on said first base member and adapted to engage and close said spray outlet; and means for sliding said first base member relative to said second base member from a first position in which said spray outlet is positioned to spray said liquid into the user's eye and a second position in which said closure means engages and closes said spray outlet.

20. An eye wash system comprising: dispensing means for dispensing an eye wash liquid through a spray outlet into a user's eye; and a nozzle housing, said spray outlet being formed on said nozzle housing, said nozzle housing comprising metering means for limiting the quantity of the liquid dispensed through said spray outlet; said metering means comprising a flexible disk having peripheral indentations, whereby when some of the eye wash liquid flows through both said indentations and said spray outlet, and the pressure of the liquid on said disk forces said disc to close, said spray outlet dispenses only a limited quantity of the eye wash liquid.

21. The eye wash system according to claim 2, wherein said nozzle has a conical end wall with said spray outlet at the apex of said conical end wall and a cylindrical chamber, the outer diameter of said disk being substantially equal to the inner diameter of said cylindrical chamber, said fluid line being adapted to dispense the eye wash liquid to said cylindrical housing.

22. The eye wash system according to claim 21, wherein said peripheral indentations have corners which are folded over towards said spray outlet to increase the springiness of said disk.

23. The eye wash system according to claim 20, wherein said metering means comprises fluid responsive biased valve means.

24. The eye wash system according to claim 23, wherein said biased valve means comprises a disk movable along a guide pin aligned with said fluid line and said spray outlet and spring means biasing said disk to close said fluid line, said disk being pushed along said guide pin by fluid in said fluid line to allow a limited quantity of said liquid to be dispensed through said spray outlet.

* * * * *